(12) United States Patent
P.M. Firouzabadi

(10) Patent No.: US 11,847,926 B2
(45) Date of Patent: Dec. 19, 2023

(54) ATTENTION-BASED NEUROFEEDBACK TRAINING

(71) Applicant: S. Mohammad P.M. Firouzabadi, Tehran (IR)

(72) Inventor: S. Mohammad P.M. Firouzabadi, Tehran (IR)

(73) Assignees: TARBIAT MODARES UNIVERSITY, Tehran (IR); S. Mohammad P. M. Firouzabadi, Tehran (IR); Zeynab Khodakarami, Tehran (IR)

( * ) Notice: Subject to any disclaimer, the term of this patent is extended or adjusted under 35 U.S.C. 154(b) by 508 days.

(21) Appl. No.: 16/776,903

(22) Filed: Jan. 30, 2020

(65) Prior Publication Data
US 2020/0168117 A1    May 28, 2020

Related U.S. Application Data

(60) Provisional application No. 62/798,518, filed on Jan. 30, 2019.

(51) Int. Cl.
G09B 19/00    (2006.01)
G08B 21/18    (2006.01)
A61B 5/00    (2006.01)
A61B 5/16    (2006.01)
A61B 5/378    (2021.01)

(52) U.S. Cl.
CPC .............. *G09B 19/00* (2013.01); *A61B 5/168* (2013.01); *A61B 5/378* (2021.01); *A61B 5/7257* (2013.01); *G08B 21/182* (2013.01)

(58) Field of Classification Search
None
See application file for complete search history.

(56) References Cited

U.S. PATENT DOCUMENTS

2018/0184935 A1\*   7/2018   Han ........................ H04W 4/38

\* cited by examiner

*Primary Examiner* — James B Hull
(74) *Attorney, Agent, or Firm* — Bajwa IP Law Firm; Haris Zaheer Bajwa

(57) ABSTRACT

A method for attention-based neurofeedback training. The method includes deriving a brain activity parameter value from a subject by providing neurofeedback training to the subject based on a training protocol, assessing an attention level of the subject simultaneously with providing the neurofeedback training, and updating the training protocol based on the attention level and the brain activity parameter value.

10 Claims, 10 Drawing Sheets

114

ATTENTION-BASED NEUROFEEDBACK TRAINING

CROSS-REFERENCE TO RELATED APPLICATION

This application claims the benefit of priority from U.S. Provisional Patent Application Ser. No. 62/798,518, filed on Jan. 30, 2019, and entitled "VISUAL ATTENTION-CONTROLLED NEUROFEEDBACK SYSTEM," which is incorporated herein by reference in its entirety.

TECHNICAL FIELD

The present disclosure generally relates to electroencephalographic signal processing, and particularly, to neurofeedback training.

BACKGROUND

Neurofeedback training is an efficient technique for treatment of different mental disorders and cognitive enhancement of healthy participants. However, this technique faces challenges including neurofeedback-illiteracy, high dependence of neurofeedback success on users' individual characteristics, long time required for neurofeedback training courses, and a relatively high financial cost. A full cognitive load may be imposed on users to find successful mental strategies for brain activity enhancement. In addition, lack of intelligence, motivation, or user's attention may lead to a prolonged treatment period or learning failure.

There is, therefore, a need for a neurofeedback training method that may assess a user's attention during neurofeedback training to enhance a training process based on user's attention. There is further a need for a neurofeedback training method that may customize the training process based on users' individual characteristics to provide a comparatively short-time and cost-efficient neurofeedback training course.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for attention-based neurofeedback training. An exemplary method may include deriving a brain activity parameter value from a subject by providing neurofeedback training to the subject based on a training protocol, assessing an attention level of the subject simultaneously with providing the neurofeedback training, and updating the training protocol based on the attention level and the brain activity parameter value.

In an exemplary embodiment, providing the neurofeedback training may include stimulating a brain of the subject by a sensory stimulus. In an exemplary embodiment, stimulating the brain of the subject by the sensory stimulus may include exposing the subject to a plurality of periodic signals. In an exemplary embodiment, each of the plurality of periodic signals may include a respective frequency of a plurality of frequencies and a respective phase of a plurality of phases.

In an exemplary embodiment, exposing the subject to the plurality of periodic signals may include displaying a plurality of time-varying images to the subject. In an exemplary embodiment, each of the plurality of time-varying images may include a respective temporal frequency larger than 30 Hz or between 3 Hz and 5 Hz.

In an exemplary embodiment, assessing the attention level may include recording an electroencephalographic (EEG) signal from the brain, extracting a plurality of features from the EEG signal, and obtaining the attention level based on the plurality of features. In an exemplary embodiment, each of the plurality of features may be associated with a respective periodic signal of the plurality of periodic signals. In an exemplary embodiment, each of the plurality of features may include a respective feature value of a plurality of feature values. An exemplary attention level may include a largest feature value of the plurality of feature values. An exemplary largest feature value may be associated with a preferred periodic signal of the plurality of periodic signals.

In an exemplary embodiment, recording the EEG signal may include attaching an EEG electrode to an occipital region of a scalp of the subject and recording a steady-state visually evoked potential (SSVEP) from the EEG electrode.

In an exemplary embodiment, extracting the plurality of features may include obtaining a frequency spectrum of the EEG signal and extracting a plurality of spectral features from the frequency spectrum. In an exemplary embodiment, obtaining the frequency spectrum may include extracting a windowed signal from the EEG signal and calculating a fast Fourier transform (FFT) of the windowed signal. An exemplary windowed signal may include a length between 4 seconds and 6 seconds.

In an exemplary embodiment, extracting the plurality of spectral features may include extracting each of the plurality of spectral features by calculating a sum of amplitudes of the frequency spectrum at first three harmonics of each respective frequency of the plurality of frequencies and calculating an inverse of each respective phase shift of a plurality of phase shifts in the frequency spectrum. In an exemplary embodiment, each of the plurality of phase shifts may be associated with a respective phase of the plurality of phases.

In an exemplary embodiment, updating the training protocol based on the attention level may include determining an attention threshold for the subject, exposing the subject to an alarm signal responsive to the attention level being lower than the attention threshold, and modifying the preferred periodic signal responsive to the attention level being equal to or higher than the attention threshold based on the brain activity parameter value.

In an exemplary embodiment, determining the attention threshold may include exposing the subject to a test periodic signal, recording a first test EEG signal from the brain simultaneously with the subject paying attention to the test periodic signal, extracting a first test feature from the first test EEG signal, obtaining an upper limit for the attention threshold, distracting the subject attention from the test periodic signal, recording a second test EEG signal from the brain simultaneously with distracting the subject attention, extracting a second test feature from the second test EEG signal, obtaining a lower limit for the attention threshold, and determining the attention threshold in a range of the lower limit and the upper limit. In an exemplary embodiment, the first test feature and the second test feature may be associated with the test periodic signal. An exemplary upper limit may include a value of the first test feature and an exemplary lower limit may include a value of the second test feature.

In an exemplary embodiment, modifying the preferred periodic signal may include removing the preferred periodic signal from the plurality of periodic signals responsive to the brain activity parameter value remaining lower than an activity threshold for a predefined period of time.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for attention-based neurofeedback training. An exemplary method may expose a subject to a sensory stimulus and may simultaneously monitor brain activity of the subject to study the effect of the sensory stimulus on the brain activity. An attention level of the subject may be extracted from electroencephalographic signals of the subject brain during a training process to determine whether the sensory stimulus is effective in enhancing the subject brain activity. If the attention level is lower than a given threshold, the subject may be urged to concentrate on the stimulus. If the attention level is high but the brain activity is low, the sensory stimulus may be modified to gain a higher brain activity. An exemplary method may lead to an individualized training with more effectiveness and may facilitate finding successful mental strategies with fewer cognitive loads on the subject.

Figure 1A:
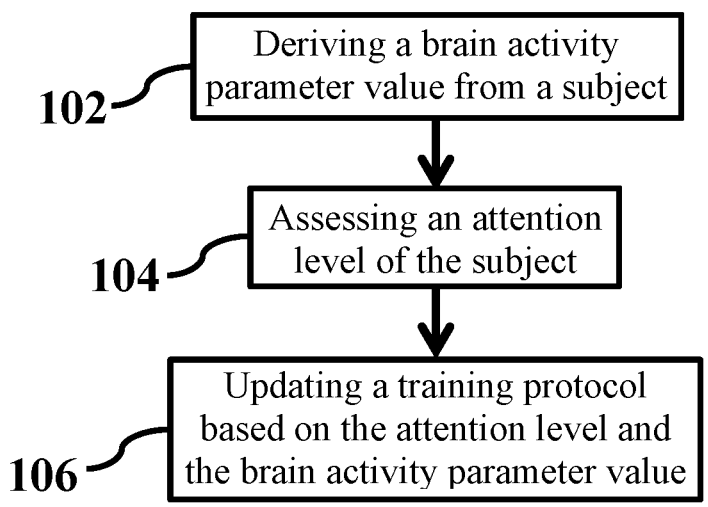
FIG. 1A shows a flowchart of a method for cache allocation to a plurality of virtual machines, consistent with one or more exemplary embodiments of the present disclosure.

FIG. 1A shows a flowchart of a method for attention-based neurofeedback training, consistent with one or more exemplary embodiments of the present disclosure. An exemplary method 100 may include deriving a brain activity parameter value from a subject by providing neurofeedback training to the subject based on a training protocol (step 102), assessing an attention level of the subject simultaneously with providing the neurofeedback training (step 104), and updating the training protocol based on the attention level and the brain activity parameter value (step 106).

Figure 2:
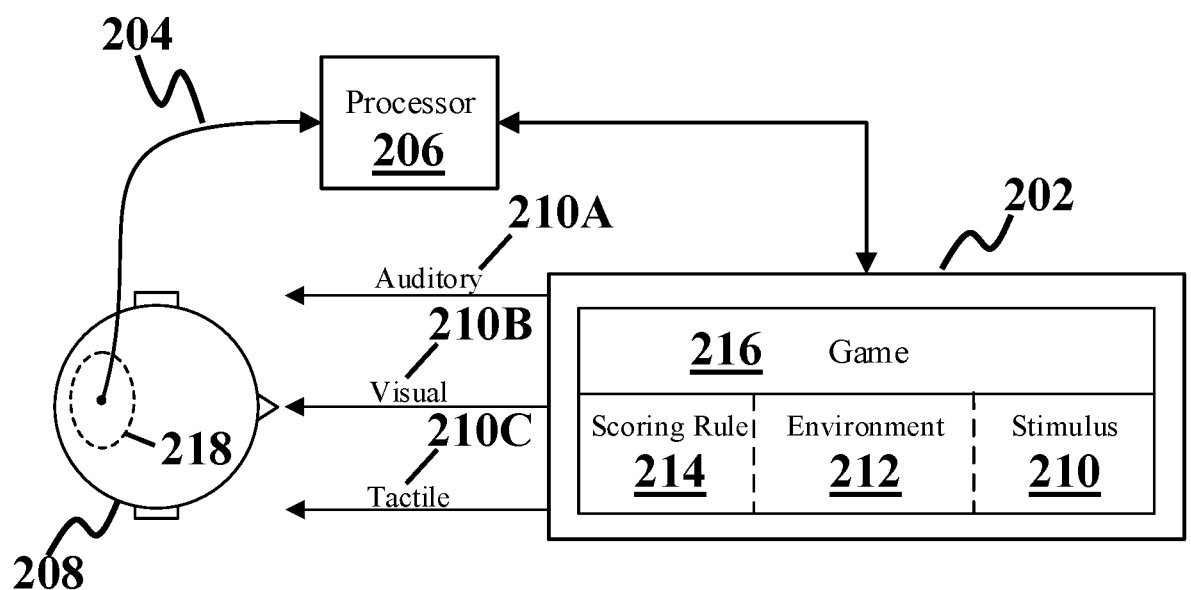
FIG. 2 shows a schematic of a system for attention-based neurofeedback training, consistent with one or more exemplary embodiments of the present disclosure.

FIG. 2 shows a schematic of a system for attention-based neurofeedback training, consistent with one or more exemplary embodiments of the present disclosure. In an exemplary embodiment, different steps of method 100 may be implemented by utilizing an exemplary system 200. In an exemplary embodiment, system 200 may include a neurofeedback training system 202, an electroencephalographic (EEG) electrode 204, and a processor 206.

For further detail with respect to step 102, in an exemplary embodiment, neurofeedback training system 202 may allow for providing neurofeedback training to a subject 208. An exemplary neurofeedback training may include stimulating a brain of subject 208 by a sensory stimulus 210. An exemplary sensory stimulus 210 may include an auditory stimulus 210A (such as an audio signal), a visual stimulus 210B (such as an image), or a tactile stimulus 210C (such as a vibrator). In an exemplary embodiment, neurofeedback training system 202 may provide a customized training environment 212 for subject 208. In an exemplary embodiment, training environment 212 may be customized based on personal characteristics of subject 208, such as intelligence, motivation, attentional control, etc. An exemplary scoring rule 214 may be set by neurofeedback training system 202 based on training environment 212. In an exemplary embodiment, scoring rule 214 may include a reward and punishment protocol for neurofeedback training. In an exemplary embodiment, a reward protocol may entail and/or be implemented in response to a gradual enhancement of brain activity (measured by the brain activity parameter value) as neurofeedback training continues. In an exemplary embodiment, a punishment protocol may entail and/or be implemented in response to no enhancement of brain activity (i.e., no considerable increase in the brain activity parameter value). In an exemplary embodiment, sensory stimulus 210, training environment 212, and scoring rule 214 may constitute a game 216 that may train brain activity of subject 208 utilizing the reward and punishment protocol.

In an exemplary embodiment, neurofeedback training system 202 may measure brain activity of subject 208 by deriving the brain activity parameter value from an EEG signal that may be recorded from the brain of subject 208 while sensory stimulus 210 is played for subject 208. In an exemplary embodiment, if the brain activity parameter value increases during training, a visual, an auditory, or a tactile reward may be given to subject 208. An exemplary reward may include continuing to play sensory stimulus 210 for subject 208. In an exemplary embodiment, if the brain activity parameter value does not increase during training, a visual, an auditory, or a tactile punishment may be given to subject 208. In an exemplary embodiment, playing sensory stimulus 210 may be paused as a punishment until the brain activity of subject 208 changes in a desired direction. During an exemplary training, subject 208 may adopt appropriate mental strategies to receive more rewards or fewer punishments.

In an exemplary embodiment, stimulating the brain of subject 208 by sensory stimulus 210, such as a set of images or audio signals, may include exposing the subject to a plurality of periodic signals. In an exemplary embodiment, each of the plurality of periodic signals may include a respective frequency of a plurality of frequencies and a respective phase of a plurality of phases. In an exemplary embodiment, each frequency of the plurality of frequencies may refer to a fundamental frequency (i.e., an inverse of a period) of a respective periodic signal. In an exemplary embodiment, each phase of the plurality of phases may refer to a phase of a frequency spectrum of a respective periodic signal at a fundamental frequency of the periodic signal.

In an exemplary embodiment, exposing subject 208 to the plurality of periodic signals may include displaying a plurality of time-varying images to the subject. An exemplary display unit (such as a monitor or an image projector) may be utilized to display time-varying images. In an exemplary embodiment, each of the plurality of time-varying images may include a respective temporal frequency larger than about 30 Hz or between about 3 Hz and about 5 Hz. In an exemplary embodiment, medium frequencies (for example, frequencies between about 5 Hz to 30 Hz) may cause rapid yet noticeable changes in displayed images which may cause disturbance in subject 208 concentration during neurofeedback training. Therefore, in an exemplary embodiment, temporal frequencies of displayed images may be set to low frequencies (for example, below 5 Hz) or high frequencies (for example, higher than 30 Hz). An exemplary time-varying image may include a flickering image (for example, an image that is flickering with a flickering frequency on a constant background), a color-varying image (i.e., a color of an exemplary image may gradually change in a cycle), or an intensity-varying image (i.e., an intensity or brightness of an exemplary image may gradually change in a cycle).

Figure 1B:
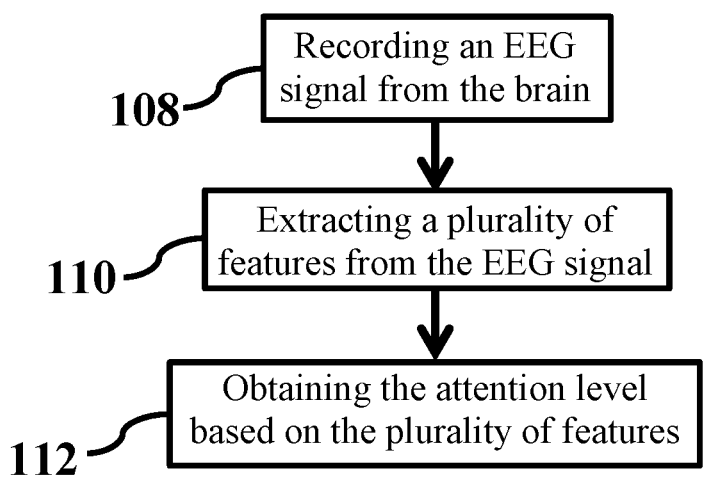
FIG. 1B shows a flowchart for assessing an attention level, consistent with one or more exemplary embodiments of the present disclosure.

In further detail with respect to step 104, FIG. 1B shows a flowchart for assessing an attention level, consistent with one or more exemplary embodiments of the present disclosure. In an exemplary embodiment, assessing the attention level of subject 208 may include recording an EEG signal from the brain (step 108), extracting a plurality of features from the EEG signal (step 110), and obtaining the attention level based on the plurality of features (step 112). In an exemplary embodiment, each of the plurality of features that may be extracted in step 108 may be associated with a respective periodic signal of the plurality of periodic signals. In an exemplary embodiment, each of the plurality of features may include a respective feature value of a plurality of feature values. An exemplary attention level may include a largest feature value of the plurality of feature values. In an exemplary embodiment, the largest feature value may be associated with a preferred periodic signal of the plurality of periodic signals.

Figure 3:
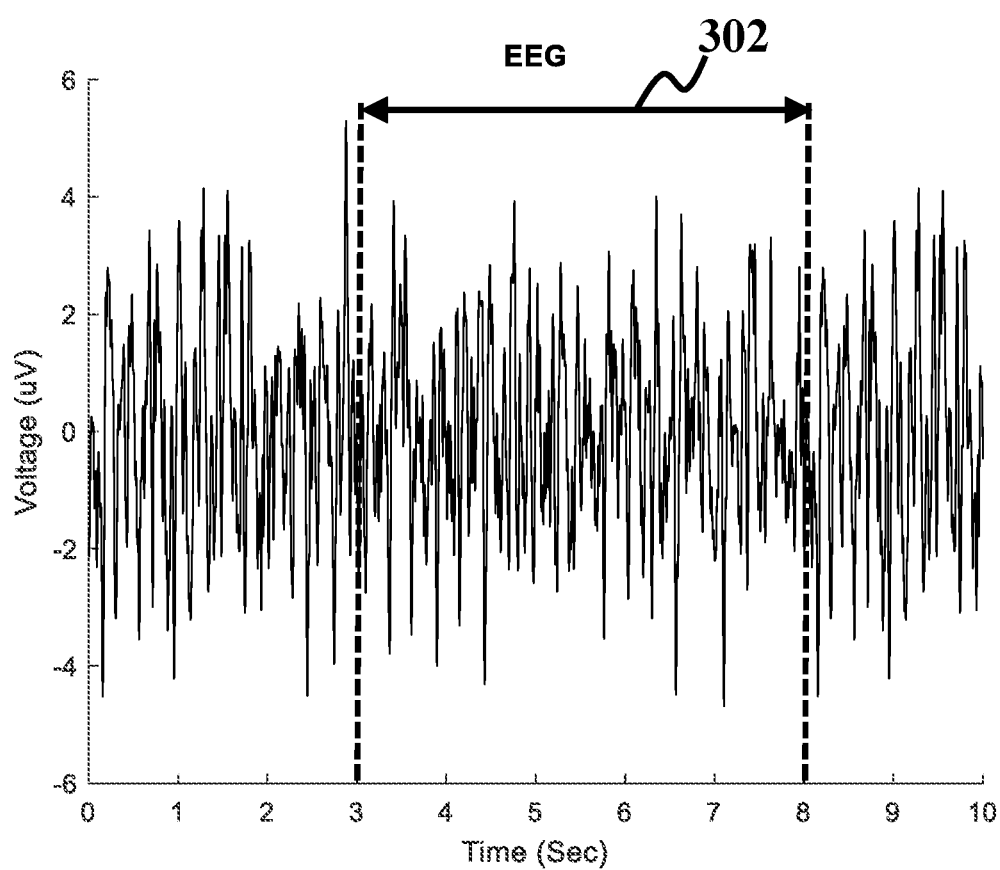
FIG. 3 shows an EEG signal, consistent with one or more exemplary embodiments of the present disclosure.

For further detail regarding step 108, FIG. 3 shows an EEG signal, consistent with one or more exemplary embodiments of the present disclosure. Referring to FIGS. 2 and 3, in an exemplary embodiment, recording an EEG signal 300 may include attaching EEG electrode 204 to a scalp of subject 208. In an exemplary embodiment, different event related potentials (ERPs) may be recorded utilizing EEG electrode 204 by attaching EEG electrode 204 to different regions of the scalp based on a type of sensory stimulus 210. For example, an auditory evoked potential may be recorded by attaching EEG electrode 204 to a frontal region of a scalp of subject 208 when auditory stimulus 210A is provided by neurofeedback training system 202. Furthermore, an exemplary somatosensory evoked potential may be recorded utilizing EEG electrode 204 from a somatosensory cortex of the brain when tactile stimulus 210C is provided by neurofeedback training system 202. In an exemplary embodiment, EEG electrode 204 may be attached to an occipital region 218 of the scalp of subject 208 to record a steady-state visually evoked potential (SSVEP) from EEG electrode 204 when visual stimulus 210B is provided by neurofeedback training system 202. In an exemplary embodiment, additional EEG electrodes may be attached to other regions of a user's scalp for neurofeedback training. In an exemplary embodiment, if an EEG signal may be recorded from a same region for neurofeedback training and assessing the attention level, a single EEG electrode may be used to provide EEG data for both neurofeedback training and attention level assessment.

Figure 1C:
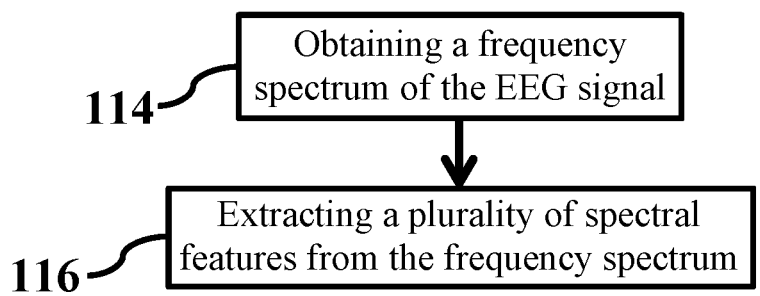
FIG. 1C shows a flowchart for extracting a plurality of features, consistent with one or more exemplary embodiments of the present disclosure.

In further detail with regards to step 110, FIG. 1C shows a flowchart for extracting a plurality of features, consistent with one or more exemplary embodiments of the present disclosure. In an exemplary embodiment, extracting the plurality of features in step 110 may include obtaining a frequency spectrum of the EEG signal (step 114) and extracting a plurality of spectral features from the frequency spectrum (step 116). In an exemplary embodiment, processor 206 may be configured to receive EEG signal 300 from EEG electrode 204 and implement step 110 to extract the plurality of features from EEG signal 300.

Figure 1D:
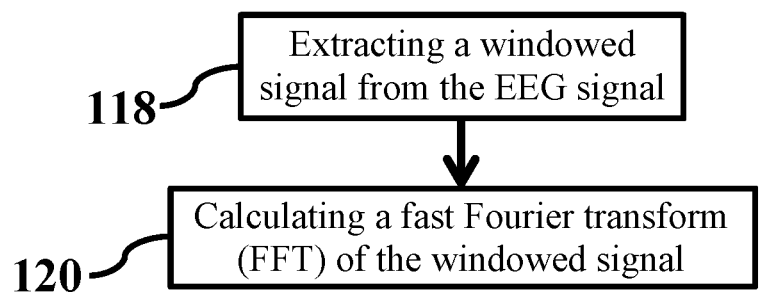
FIG. 1D shows a flowchart for obtaining a frequency spectrum of an electroencephalographic (EEG) signal, consistent with one or more exemplary embodiments of the present disclosure.

For further detail with respect to step 114, FIG. 1D shows a flowchart for obtaining a frequency spectrum of an EEG signal, consistent with one or more exemplary embodiments of the present disclosure. In an exemplary embodiment, obtaining the frequency spectrum may include extracting a windowed signal from the EEG signal (step 118) and calculating a fast Fourier transform (FFT) of the windowed signal (step 120).

Referring again to FIG. 3, in further detail with regards to step 118, an exemplary windowed signal 302 may be extracted from EEG signal 300 by multiplying an amplitude of EEG signal 300 by a respective amplitude of a rectangular function at each point of time. An exemplary temporal length of windowed signal 302 may be determined by determining a length of an exemplary rectangular function. In an exemplary embodiment, if the length of the rectangular function is too short, windowed signal 302 may fail to provide enough information for an appropriate attention level assessment. On the other hand, in an exemplary embodiment, if the length of the rectangular function is too long, attention level assessment may not be carried out in real-time. Therefore, a suitable value of an exemplary temporal length may provide accurate information for neuro-feedback training in real-time so that a training procedure may be enhanced as the training procedure continues. In an exemplary embodiment, windowed signal 302 may include a length between about 4 seconds and about 6 seconds. In an exemplary embodiment, the well-known FFT algorithm may be utilized in step 120 to obtain the frequency spectrum of windowed signal 302 in real-time.

Figure 4:
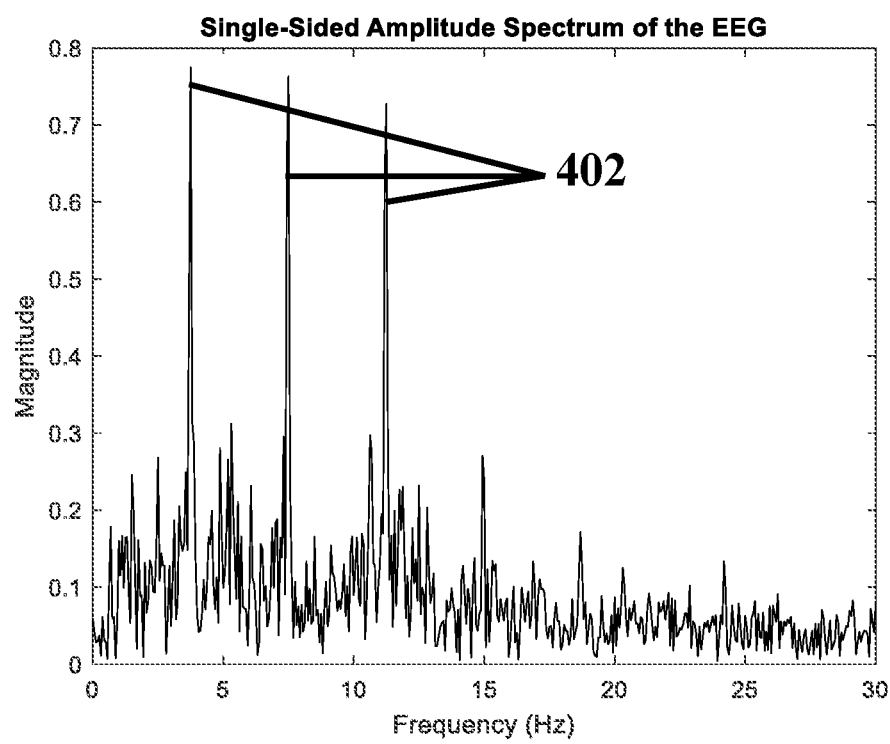
FIG. 4 shows a frequency spectrum, consistent with one or more exemplary embodiments of the present disclosure.

FIG. 4 shows a frequency spectrum, consistent with one or more exemplary embodiments of the present disclosure. Referring to FIGS. 1B and 4, in an exemplary embodiment, extracting the plurality of spectral features (step 116) may include extracting each of the plurality of spectral features by calculating a sum of amplitudes of a frequency spectrum 400 at first three harmonics 402 of each respective frequency of the plurality of frequencies. In an exemplary embodiment, first three harmonics 402 may include a first harmonic (i.e., a fundamental frequency of a periodic signal), a second harmonic (i.e., twice of a fundamental frequency of a periodic signal), and a third harmonic (i.e., three times of a fundamental frequency of a periodic signal). In an exemplary embodiment, amplitudes of first three harmonics 402 may be significantly larger than amplitudes of other frequencies in frequency spectrum 400. In other words, in an exemplary embodiment, first three harmonics 402 may effectively distinguish a signal that is gaining attention of subject 208 from other signals that may be provided by sensory stimulus 210. Therefore, in an exemplary embodiment, the sum of first three harmonics 402 may serve well as a feature for assessing the attention level of subject 208. A higher value for the sum of first three harmonics 402 may imply that a signal associated with first three harmonics 402 may have gained more attention from subject 208. Therefore, in an exemplary embodiment, a periodic signal with a fundamental frequency that may correspond to a highest sum of first three harmonics in a frequency spectrum of EEG signal 300 may be selected as a preferred periodic signal (i.e., a signal that may have gained a highest attention of subject 208 among all of the plurality of periodic signals) and the attention level may be set to the corresponding sum of first three harmonics.

In an exemplary embodiment, extracting the plurality of spectral features (step 116) may also include calculating an inverse of each respective phase shift of a plurality of phase shifts in frequency spectrum 400. In an exemplary embodiment, each of the plurality of phase shifts may be associated with a respective phase of the plurality of phases. An exemplary phase shift may refer to a difference of a phase of frequency spectrum 400 and a phase of a periodic signal at a fundamental frequency of the periodic signal. In an exemplary embodiment, a lower phase shift at a fundamental frequency may imply a higher similarity between frequency spectrum 400 and a periodic signal associated with the fundamental frequency. Therefore, in an exemplary embodiment, a periodic signal with a fundamental frequency that may correspond to a lowest phase shift in a frequency spectrum of EEG signal 300 may be selected as a preferred periodic signal and the attention level may be set to the inverse the corresponding phase shift.

Referring again to FIGS. 1B and 2, in an exemplary embodiment, step 112 may include obtaining the attention level based on the plurality of features. In an exemplary embodiment, processor 206 may be configured to implement step 112. In an exemplary embodiment, a feature with a largest feature value among the plurality of feature values may be selected as a preferred feature. In an exemplary embodiment, the largest feature value may be assigned to the attention level. In an exemplary embodiment, a periodic signal corresponding to the preferred feature may be selected as the preferred periodic signal. In an exemplary embodiment, the largest feature value may include a sum of first three harmonics of a fundamental frequency of the preferred periodic signal, an inverse of a phase shift at the fundamental frequency of the preferred periodic signal in frequency spectrum 400, or a combination of the sum of the first three harmonics (such as first three harmonics 402) and the phase shift. In an exemplary embodiment, the sum of first three harmonics 402 may be selected as a feature for determining the value of the attention level when each of the plurality of periodic signals has a different fundamental frequency. In an exemplary embodiment, the phase shift may be selected as a feature for determining the value of the attention level when the plurality of periodic signals may have similar fundamental frequencies but have different phases. In an exemplary embodiment, a combination of the phase shift and the sum of the first three harmonics may be used for determining the value of the attention level when each of the plurality of periodic signals may have a different phase and frequency. Furthermore, in an exemplary embodiment, a periodic signal with a highest sum of first three harmonics and a lowest phase shift among all of the plurality of periodic signals may be selected as the preferred signal.

Figure 1E:
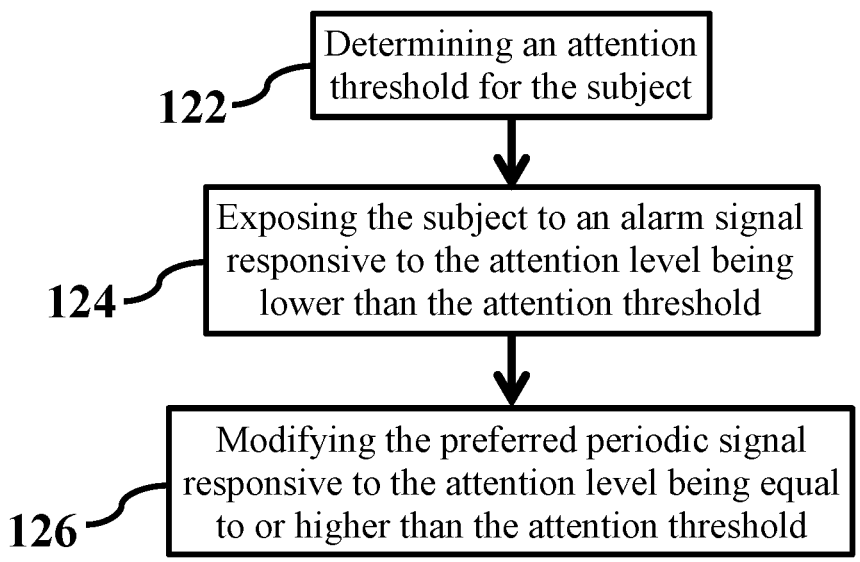
FIG. 1E shows a flowchart for updating a training protocol, consistent with one or more exemplary embodiments of the present disclosure.

Referring again to FIG. 1A, in an exemplary embodiment, step 106 may include updating the training protocol based on the attention level. For further detail with respect to step 106, FIG. 1E shows a flowchart for updating a training protocol, consistent with one or more exemplary embodiments of the present disclosure. In an exemplary embodiment, updating the training protocol may include determining an attention threshold for the subject (step 122), exposing the subject to an alarm signal responsive to the attention level being lower than the attention threshold (124), and modifying the preferred periodic signal responsive to the attention level being equal to or higher than the attention threshold based on the brain activity parameter value (step 126).

Figure 1F:
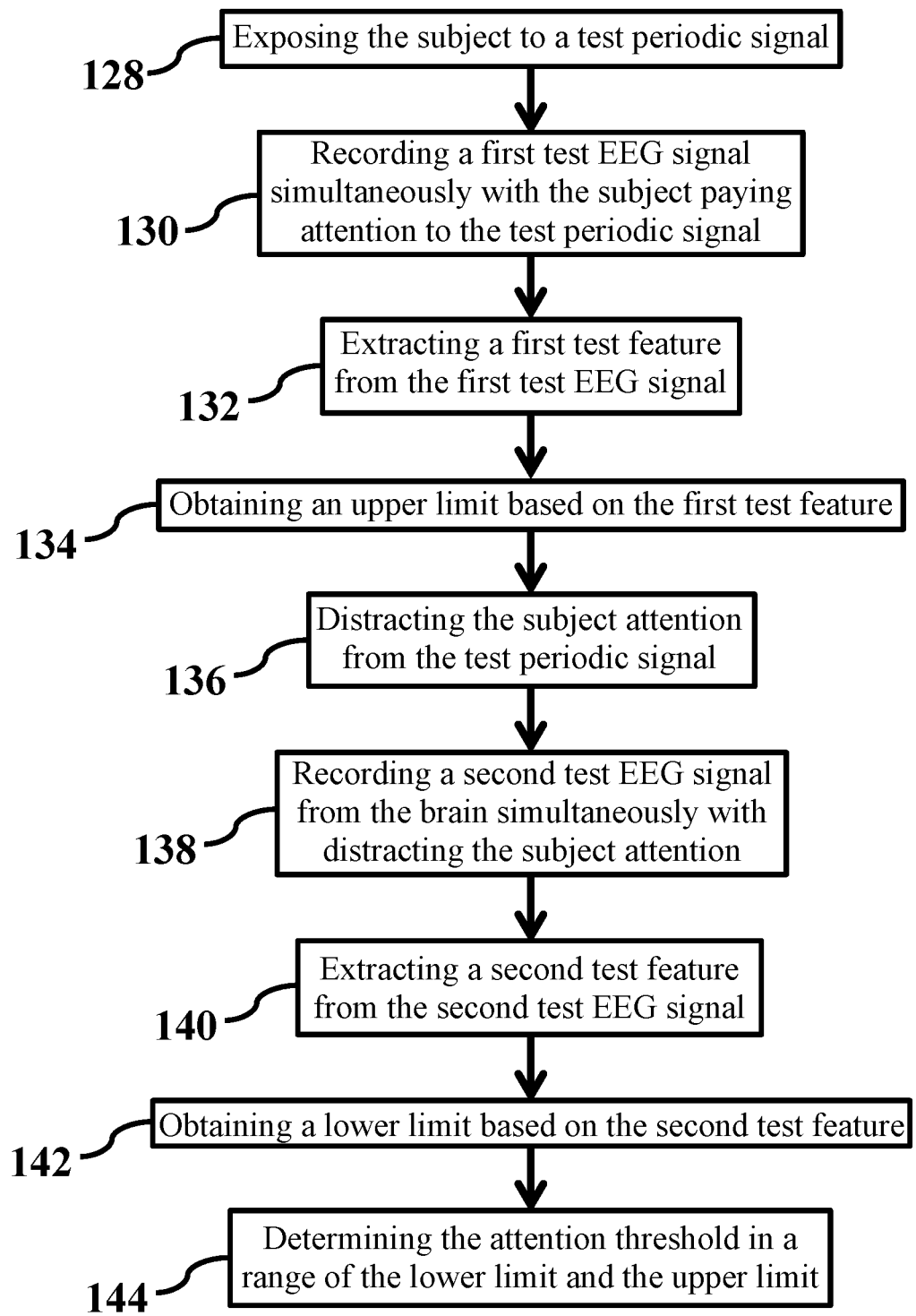
FIG. 1F shows a flowchart for determining an attention threshold, consistent with one or more exemplary embodiments of the present disclosure.

In further detail with respect to step 122, FIG. 1F shows a flowchart for determining an attention threshold, consistent with one or more exemplary embodiments of the present disclosure. In an exemplary embodiment, determining the attention threshold may include exposing the subject to a test periodic signal (step 128), recording a first test EEG signal from the brain simultaneously with the subject paying attention to the test periodic signal (step 130), extracting a first test feature from the first test EEG signal (step 132), obtaining an upper limit for the attention threshold based on the first test feature (step 134), distracting the subject attention from the test periodic signal (step 136), recording a second test EEG signal from the brain simultaneously with distracting the subject attention (step 138), extracting a second test feature from the second test EEG signal (step 140), obtaining a lower limit for the attention threshold based on the second test feature (step 142), and determining the attention threshold in a range of a lower limit and an upper limit (step 144). In an exemplary embodiment, the first test feature and the second test feature may be associated with the test periodic signal.

For further detail with respect to step 128, in an exemplary embodiment, exposing subject 208 to a test periodic signal may be similar to exposing subject 208 to the plurality of periodic signals in step 102. In an exemplary embodiment, any of the plurality of periodic signals may be selected as the test periodic signal.

In further detail with regards to step 130, in an exemplary embodiment, subject 208 may be requested by an operator of neurofeedback training system 202 to pay attention to the test periodic signal while being exposed to the test periodic signal. In an exemplary embodiment, subject 208 may be assisted in concentrating on the test periodic signal by removing other possible sensory stimuli from a training environment. In an exemplary embodiment, further detail regarding the recording of the first test EEG signal during the subject concentration on the test periodic signal may be similar to recording the EEG signal discussed in step 108.

In further detail regarding step 132, in an exemplary embodiment, extracting the first test feature from the first test EEG signal may be similar to extracting each of the plurality of features in step 110. In an exemplary embodiment, a type of the first test feature may be the same as a type of the plurality of features. For example, if the plurality of features include a sum of amplitudes of a frequency spectrum of EEG signal 300, the first test feature may include a corresponding sum of amplitudes of a frequency spectrum of the first test EEG signal. As another example, if the plurality of features include a phase of EEG signal 300 at a given frequency, the first test feature may include a corresponding phase of the first test EEG signal at the given frequency. Further details with regards to the first test feature may be analogous to details regarding each of the plurality of features discussed in step 116.

In further detail with regards to step 134, in an exemplary embodiment, the upper limit of the attention threshold may include a value of the first test feature. In an exemplary embodiment, since the first test feature is obtained simultaneously with subject 208 paying attention to the test periodic signal, it may be assumed that an impact of the test periodic signal on the first test EEG signal may be observable in the first test feature. Moreover, in an exemplary embodiment, a high level of attention may be obtained from the first test feature since the first test EEG signal may be recorded while subject 208 concentrates on the test periodic signal. Therefore, in an exemplary embodiment, the value of the first test feature may be considered an upper limit for the attention level of subject 208.

For further detail with respect to step 136, in an exemplary embodiment, the subject attention may be distracted from the test periodic signal by removing the test periodic signal. In an exemplary embodiment, subject 208 may further be requested to relax (i.e., not concentrate on a particular subject) for a limited time. In an exemplary embodiment, distracting the subject attention may reduce the attention level of subject 208. Therefore, in an exemplary embodiment, obtaining a value of the attention level while the subject attention is distracted may provide a lower limit for the attention level. To obtain the value of the attention level, in an exemplary embodiment, step 138 may be implemented to record the second test EEG signal while the subject attention is being distracted. Next, an exemplary second test feature may be extracted from the second test EEG signal in step 140 (similar to step 132) which may include a low level of attention. Consequently, an exemplary lower limit of the attention limit may be obtained in step 142 by setting the lower limit to a value of the second test feature. Finally, an exemplary attention threshold may be determined by setting the attention threshold to a value between the lower limit and the upper limit. In an exemplary embodiment, an average of the lower limit and the upper limit may be determined as the attention threshold.

Referring again to FIG. 1E, in an exemplary embodiment, the attention threshold may be utilized to determine whether subject 208 is paying attention to any of sensory stimuli (for example, any of the plurality of periodic signals) that may be provided by neurofeedback training system 202. In further detail regarding step 124, in an exemplary embodiment, if the subject attention level (that is obtained from the plurality of features) becomes lower than the attention threshold, it may be inferred that subject 208 is no longer paying enough attention to any of the plurality of periodic signals. Therefore, subject 208 may be exposed to an exemplary alarm signal if the attention level becomes lower than the attention threshold. In an exemplary embodiment, the alarm signal may be generated by flashing a light, making a sound, modifying the stimuli (for example, changing a size of a displayed image), touching subject 208, etc. In an exemplary embodiment, any signal that may help refocusing the subject concentration on the stimuli provided by neurofeedback training system 202 may be utilized as an alarm signal.

For further detail with regards to step 126, in an exemplary embodiment, the attention level may be utilized to modify a preferred periodic signal. In an exemplary embodiment, if the attention level becomes higher that the attention threshold, it may be inferred that subject 208 is concentrating on the preferred periodic signal (which may be obtained utilizing the attention level, as discussed in step 112). This information, along with the brain activity parameter which may be derived by neurofeedback training system 202 in step 102, may be utilized to update the training protocol to enhance the training procedure. In an exemplary embodiment, processor 206 may be configured to receive the brain activity parameter from neurofeedback training system 202 and utilize the brain activity parameter together with the attention level to update the training protocol.

In an exemplary embodiment, if the brain activity parameter shows an increasing trend (for example, gradually increasing as neurofeedback training continues), it may be inferred that the preferred periodic signal is appropriate for neurofeedback training. Therefore, in an exemplary embodiment, a remaining of neurofeedback training may be dominated by the preferred periodic signal, i.e., other periodic signals may be removed from sensory stimulus 210, a size of the preferred periodic signal may be increased (if the preferred periodic signal includes an image), a volume of the preferred periodic signal may be increased (if the preferred periodic signal includes audio), or new signals similar to the preferred periodic signal may be generated to serve as sensory stimuli.

In an exemplary embodiment, modifying the preferred periodic signal may include removing the preferred periodic signal from the plurality of periodic signals responsive to the brain activity parameter value remaining lower than an activity threshold for a predefined period of time that may be determined by an operator of neurofeedback training system 202 based on the subject 208 personal characteristics and mental health conditions. In an exemplary embodiment, the activity threshold may be determined based on variations of the brain activity parameter value. For example, an initial value of the brain activity parameter value or an average value of the brain activity parameter value in a given period of time may be selected as the activity threshold. In an exemplary embodiment, a trend of the brain activity parameter value may be determined based on the activity threshold. In an exemplary embodiment, if the brain activity parameter value remains lower than the activity threshold, it may be inferred that the preferred periodic signal may not have an increasing trend, and therefore, it may not be appropriate for neurofeedback training. Consequently, in an exemplary embodiment, the preferred periodic signal may be removed from the plurality of periodic signals and neurofeedback training may continue with a remaining of the plurality of periodic signals.

Figure 5:
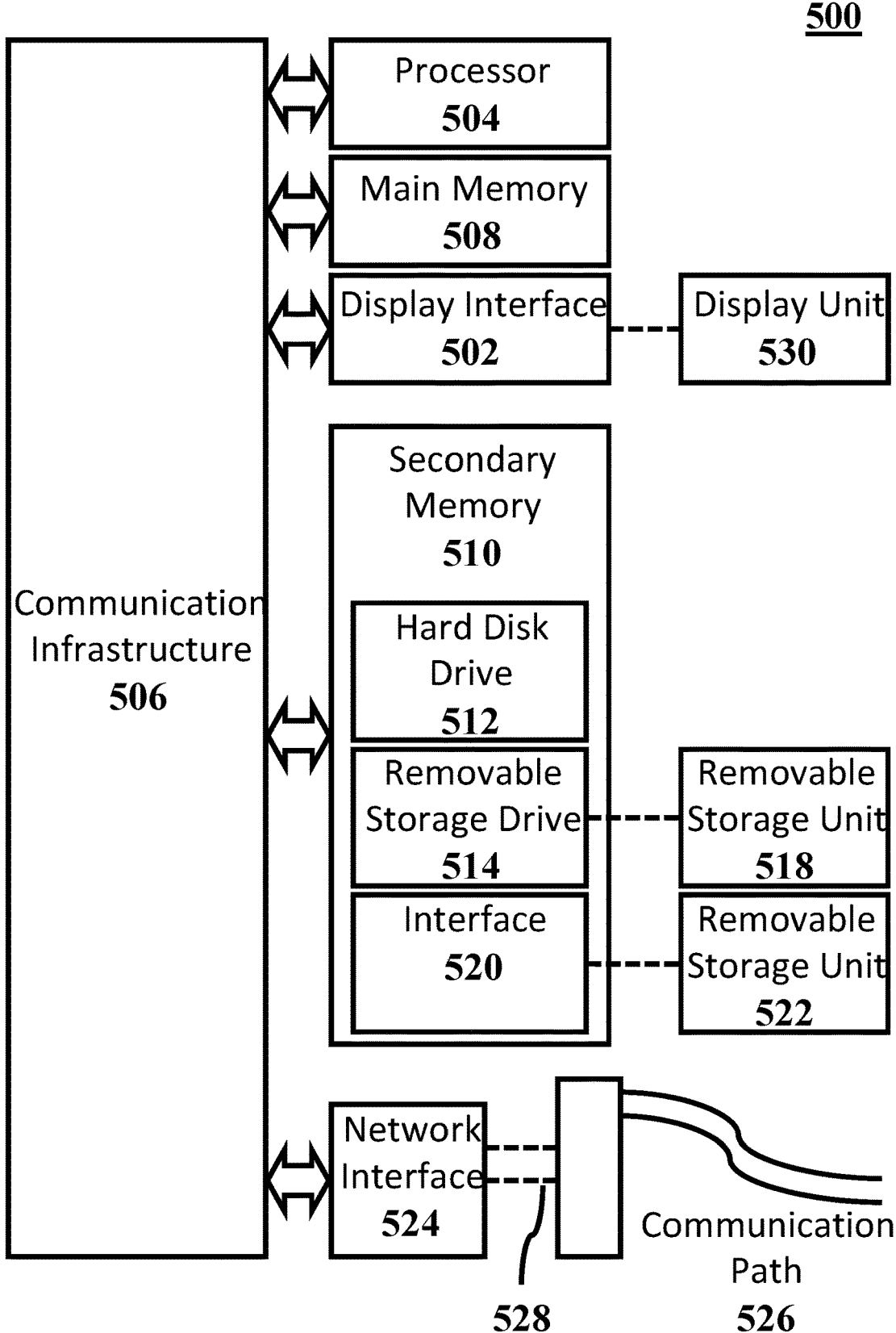
FIG. 5 shows a high-level functional block diagram of a computer system, consistent with one or more exemplary embodiments of the present disclosure.

FIG. 5 shows an example computer system 500 in which an embodiment of the present invention, or portions thereof, may be implemented as computer-readable code, consistent with exemplary embodiments of the present disclosure. For example, method 100 may be implemented in computer system 500 using hardware, software, firmware, tangible computer readable media having instructions stored thereon, or a combination thereof and may be implemented in one or more computer systems or other processing systems. In an exemplary embodiment, system 500 may be analogous to processor 206. Hardware, software, or any combination of such may embody any of the modules and components in FIGS. 1A-1F and 2.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in method 100 illustrated by flowchart 100 of FIG. 1A and flowchart 112 of FIG. 1B discussed above. Accordingly, such computer programs represent controllers of computer system 500. Where an exemplary embodiment of method 100 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for attention-based neurofeedback training, the method comprising:
   providing neurofeedback training to a subject based on a training protocol by exposing the subject to a plurality of periodic signals, each of the plurality of periodic signals comprising a respective frequency of a plurality of frequencies and a respective phase of a plurality of phases;
   deriving, utilizing one or more processors, a brain activity parameter value based on a value of a signal captured from the subject responsive to providing the neurofeedback training to the subject;
   assessing, utilizing the one or more processors, an attention level of the subject simultaneously with providing the neurofeedback training, comprising:
      recording an electroencephalographic (EEG) signal from a brain of the subject;
      extracting, utilizing the one or more processors, a plurality of features from the EEG signal, each of the plurality of features associated with a respective periodic signal of the plurality of periodic signals, each of the plurality of features comprising a respective feature value of a plurality of feature values; and obtaining, utilizing the one or more processors, the attention level based on the plurality of features, the attention level comprising a largest feature value of the plurality of feature values, the largest feature value associated with a preferred periodic signal of the plurality of periodic signals; and updating, utilizing the one or more processors, the training protocol based on the attention level and the brain activity parameter value.

2. The method of claim 1, wherein updating the training protocol based on the attention level and the brain activity parameter value comprises:

determining an attention threshold for the subject;

exposing the subject to an alarm signal responsive to the attention level being lower than the attention threshold; and modifying the preferred periodic signal responsive to the attention level being equal to or higher than the attention threshold based on the brain activity parameter value.

3. The method of claim 2, wherein determining the attention threshold comprises:

exposing the subject to a test periodic signal;

recording a first test EEG signal from the brain simultaneously with the subject paying attention to the test periodic signal;

extracting, utilizing the one or more processors, a first test feature from the first test EEG signal, the first test feature associated with the test periodic signal;

obtaining, utilizing the one or more processors, an upper limit for the attention threshold, the upper limit comprising a value of the first test feature;

distracting the subject attention from the test periodic signal;

recording a second test EEG signal from the brain simultaneously with distracting the subject attention;

extracting, utilizing the one or more processors, a second test feature from the second test EEG signal, the second test feature associated with the test periodic signal;

obtaining, utilizing the one or more processors, a lower limit for the attention threshold, the lower limit comprising a value of the second test feature; and determining the attention threshold in a range of the lower limit and the upper limit.

4. The method of claim 2, wherein modifying the preferred periodic signal comprises removing the preferred periodic signal from the plurality of periodic signals responsive to the brain activity parameter value remaining lower than a brain activity threshold for a predefined period of time.

5. The method of claim 1, wherein extracting the plurality of features comprises:

obtaining a frequency spectrum of the EEG signal; and extracting a plurality of spectral features from the frequency spectrum.

6. The method of claim 5, wherein obtaining the frequency spectrum comprises:

extracting a windowed signal from the EEG signal, the windowed signal comprising a length between 4 seconds and 6 seconds; and calculating a fast Fourier transform (FFT) of the windowed signal.

7. The method of claim 5, wherein extracting the plurality of spectral features comprises extracting each of the plurality of spectral features by:

calculating a sum of amplitudes of the frequency spectrum at first three harmonics of each respective frequency of the plurality of frequencies; and calculating an inverse of each respective phase shift of a plurality of phase shifts in the frequency spectrum, each of the plurality of phase shifts associated with a respective phase of the plurality of phases.

8. The method of claim 1, wherein exposing the subject to the plurality of periodic signals comprises displaying a plurality of time-varying images to the subject, each of the plurality of time-varying images comprising a respective temporal frequency larger than 30 Hz or between 3 Hz and 5 Hz.

9. The method of claim 8, wherein recording the EEG signal comprises:

attaching an EEG electrode to an occipital region of a scalp of the subject; and recording a steady-state visually evoked potential (SS-VEP) from the EEG electrode.

10. A method for attention-based neurofeedback training, the method comprising:

providing neurofeedback training to a subject based on a training protocol by exposing the subject to a plurality of periodic signals, each of the plurality of periodic signals comprising a respective frequency of a plurality of frequencies and a respective phase of a plurality of phases;

determining, utilizing one or more processors, a brain activity parameter value based on a value of a signal captured from the subject responsive to providing the neurofeedback training to the subject;

assessing, utilizing the one or more processors, an attention level of the subject simultaneously with providing the neurofeedback training, comprising:

recording an electroencephalographic (EEG) signal from a brain of the subject;

extracting, utilizing the one or more processors, a plurality of features from the EEG signal, each of the plurality of features associated with a respective periodic signal of the plurality of periodic signals, each of the plurality of features comprising a respective feature value of a plurality of feature values; and obtaining, utilizing the one or more processors, the attention level based on the plurality of features, the attention level comprising a largest feature value of the plurality of feature values, the largest feature value associated with a preferred periodic signal of the plurality of periodic signals; and updating, utilizing the one or more processors, the training protocol based on the attention level and the brain activity parameter value.

* * * * *